US010674933B2

(12) United States Patent
Gliner et al.

(10) Patent No.: US 10,674,933 B2
(45) Date of Patent: Jun. 9, 2020

(54) ENLARGEMENT OF TRACKING VOLUME BY MOVEMENT OF IMAGING BED

(71) Applicant: BIOSENSE WEBSTER (ISRAEL) LTD., Yokneam (IL)

(72) Inventors: Vadim Gliner, Haifa (IL); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 632 days.

(21) Appl. No.: 14/520,665

(22) Filed: Oct. 22, 2014

(65) Prior Publication Data
US 2016/0113723 A1    Apr. 28, 2016

(51) Int. Cl.
| | |
|---|---|
| A61B 5/00 | (2006.01) |
| A61B 5/055 | (2006.01) |
| A61B 5/06 | (2006.01) |
| A61B 34/20 | (2016.01) |
| G01R 33/563 | (2006.01) |
| A61B 6/04 | (2006.01) |
| A61M 25/01 | (2006.01) |

(Continued)

(52) U.S. Cl.
CPC ............ A61B 5/0555 (2013.01); A61B 5/062 (2013.01); A61B 5/066 (2013.01); A61B 5/6852 (2013.01); A61B 6/0457 (2013.01); A61B 34/20 (2016.02); A61M 25/0127 (2013.01); G01R 33/287 (2013.01); G01R 33/56375 (2013.01); A61B 2090/3762 (2016.02); A61B 2562/04 (2013.01); A61M 2025/0166 (2013.01)

(58) Field of Classification Search
CPC ............................. A61B 5/0555; A61B 5/062
See application file for complete search history.

(56) References Cited

U.S. PATENT DOCUMENTS 7,738,944 B2    6/2010  Ho et al.
2004/0044279 A1*  3/2004  Lewin ................ G01R 33/4833
                                                      600/407

(Continued)

FOREIGN PATENT DOCUMENTS

EP    1362550 A1    11/2003
EP    2722018 A2    4/2014

(Continued)

OTHER PUBLICATIONS

European Patent Search 15190778.9, Filed on Apr. 8, 2016.

(Continued)

*Primary Examiner* — Joseph M Santos Rodriguez

(57) ABSTRACT

A medical system, includes an imaging apparatus, which includes an array of detectors, which define an imaging volume and form images of a region within a body of a patient that is positioned in the imaging volume. A movable bed transports the body of the patient through the imaging volume. An invasive probe is inserted into a lumen within the body of the patient. A tracking apparatus includes a field transducer positioned in the imaging apparatus and defining a tracking volume within the imaging apparatus, and generates an indication of a location of the invasive probe within the tracking volume responsively to an interaction between the field transducer and the invasive probe. A controller controls the movable bed in response to the location of the invasive probe indicated by the tracking apparatus.

26 Claims, 3 Drawing Sheets

(51) Int. Cl.
    *G01R 33/28*     (2006.01)
    *A61B 90/00*     (2016.01)

(56)                References Cited

U.S. PATENT DOCUMENTS

2004/0097806 A1*  5/2004  Hunter .............. A61B 1/00071
                                                          600/434
2009/0177076 A1   7/2009  Aldefeld
2014/0094684 A1   4/2014  Govari et al.

FOREIGN PATENT DOCUMENTS

EP         2737869 A1    6/2014
JP        H07194616 A    8/1995
JP        2008178686 A   8/2008
JP        2014089186 A   5/2014
WO        WO 96/05768    2/1996

OTHER PUBLICATIONS

U.S. Appl. No. 14/195,068, filed Mar. 3, 2014.
U.S. Appl. No. 14/138,654, filed Dec. 23, 2013.
Notification of Reasons for Refusal; Patent Application 2015-0206980; dated Jul. 11, 2019.
Australia Examination Report No. 2 for standard patent application, Application No. AU 2015243011, dated Dec. 3, 2019.

* cited by examiner

ENLARGEMENT OF TRACKING VOLUME BY MOVEMENT OF IMAGING BED

FIELD OF THE INVENTION

The present invention relates generally to tracking invasive probes within the body of a patient, and specifically to apparatus and methods for tracking probe location within a body in a tomographic imaging system.

BACKGROUND

Medical tomographic imaging involves capturing radiation transmitted through or emitted from the patient's body in multiple directions, and then processing the captured radiation to reconstruct images of structures within the body, typically in three dimensions. Modern tomographic imaging techniques include, inter alia, computed tomography (CT) based on X-ray transmission and magnetic resonance imaging (MRI), as well as single-photon emission computed tomography (SPECT) using gamma rays, positron emission tomography (PET), and other methods that are known in the art.

In a typical medical tomographic imaging system, the patient lies on a motorized bed (also referred to as a table), which conveys the patient through the bore of the imaging system. The system generally controls the motion of the bed precisely, either automatically or under operator control, in order to position the part of the body that is of interest within the detection volume of the system. In some applications, the bed moves continuously at a controlled speed during imaging, as described, for example, in U.S. Pat. No. 7,738,944.

Magnetic sensing systems are widely used for tracking the position of a probe inside the body of a patient. For example, PCT International Publication WO 1996/05768, whose disclosure is incorporated herein by reference, describes a locating system in which a plurality of field generators produce AC magnetic fields, which are detected by a plurality of sensors at the distal end of an invasive medical instrument. Signals from the sensors are processed in order to find the location and orientation coordinates of the instrument. The CARTO® system, produced by Biosense Webster (Diamond Bar, Calif.), uses this sort of magnetic sensing to track and visualize the location of a catheter inside the patient's body.

Magnetic sensing of catheter position may be used in conjunction with imaging modalities, such as MRI. For example, U.S. Patent Application Publication 2014/0094684, whose disclosure is incorporated herein by reference, describes a medical probe that is suitable for operating in an MRI environment. The probe comprises a flexible insertion tube, which has a distal end for insertion into a body cavity, such as a section of a heart, which is imaged using MRI techniques. A coil in the probe may be used as a position sensor to derive the location and orientation of the distal end of the probe from signals generated when the coil is in an alternating magnetic field having a known spatial distribution. This magnetic field is generated by coils placed at known positions, typically below the patient's torso.

SUMMARY

Embodiments of the present invention provide improved methods and apparatus for tracking the location of an invasive probe in a patient's body.

There is therefore provided, in accordance with an embodiment of the present invention, a medical system, including an imaging apparatus, which includes an array of detectors, which define an imaging volume and are configured to form images of a region within a body of a patient that is positioned in the imaging volume, and a movable bed, which is configured to transport the body of the patient through the imaging volume. An invasive probe is configured for insertion into a lumen within the body of the patient. A tracking apparatus includes a field transducer positioned in the imaging apparatus and defining a tracking volume within the imaging apparatus, and is configured to generate an indication of a location of the invasive probe within the tracking volume responsively to an interaction between the field transducer and the invasive probe. A controller is coupled to control the movable bed in response to the location of the invasive probe indicated by the tracking apparatus.

In a disclosed embodiment, the imaging apparatus includes magnetic resonance imaging (MRI) apparatus, and the detectors include coils configured to receive signals from tissues in the body in response to an applied magnetic field. The invasive probe may include a catheter, which is configured for insertion through a blood vessel into a heart of the patient.

In some embodiments, the field transducer includes a location pad, including a plurality of coils, which generate magnetic fields within the tracking volume, and the tracking apparatus is configured to receive signals output from the invasive probe in response to the magnetic fields and to process the signals in order to generate the indication of the location of the invasive probe. The field transducer is typically positioned so that the tracking volume overlaps the imaging volume, and the controller is configured to register the location of the invasive probe in a coordinate system of the imaging apparatus and to superimpose the indication of the registered location on the images that are produced by the imaging apparatus.

In some embodiments, the field transducer is positioned so that the tracking volume is fixed relative to the imaging volume, and wherein the controller is configured to cause the movable bed to shift in response to motion of the invasive probe within the body of the patient so that the invasive probe remains within the imaging volume notwithstanding the motion. The controller may be configured to cause the movable bed to shift in a direction opposite to the motion of the invasive probe and possibly to control a speed of movement of the movable bed so as to compensate for advancement of the invasive probe through the body.

There is also provided, in accordance with an embodiment of the present invention, a method for imaging and tracking, which includes positioning a field transducer of a tracking apparatus in an imaging apparatus, which has an imaging volume and forms images of a region within a body of a patient that is positioned in the imaging volume while the patient lies on a movable bed, which transports the body of the patient through the imaging volume. A location of an invasive probe that has been inserted into a lumen in the body of the patient is tracked responsively an interaction between the field transducer and the invasive probe while the invasive probe is within a tracking volume of the tracking apparatus that is defined by the field transducer. The movable bed is controlled in response to the tracked location of the invasive probe.

There is additionally provided, in accordance with an embodiment of the present invention, tracking apparatus for operation in conjunction with an imaging apparatus, which has an imaging volume and is configured to form images of a region within a body of a patient that is positioned in the imaging volume, and which includes a movable bed for transporting the body of the patient through the imaging volume. The tracking apparatus includes an invasive probe configured for insertion into a lumen within the body of the patient. A field transducer is positioned in the imaging apparatus and defines a tracking volume within the imaging apparatus. A controller is configured to generate an indication of a location of the invasive probe within the tracking volume responsively to an interaction between the field transducer and the invasive probe, and to control the movable bed in response to the location of the invasive probe.

The present invention will be more fully understood from the following detailed description of the embodiments thereof, taken together with the drawings in which:

DETAILED DESCRIPTION OF EMBODIMENTS

Figure 1:
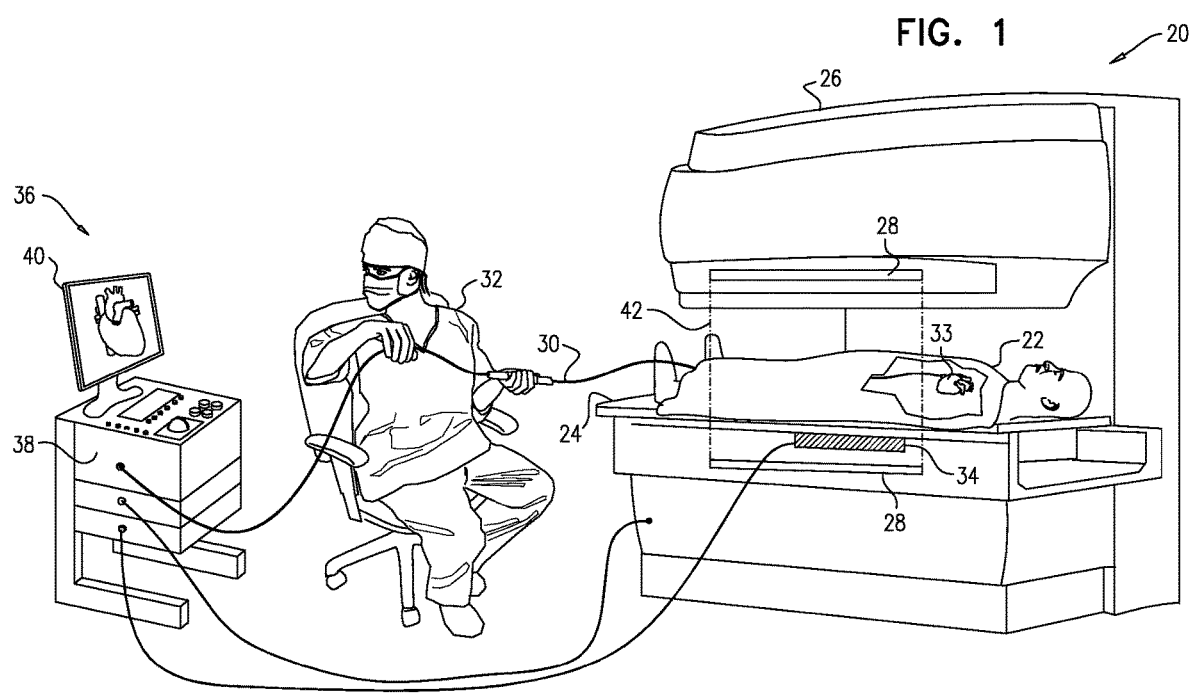
FIG. 1 is schematic pictorial illustration of an imaging and tracking system, in accordance with an embodiment of the present invention.

In some new modalities of image-guided medical treatment, an invasive probe, such as a catheter, is inserted into and manipulated within a patient's body while an imaging apparatus, such as an MRI system, captures images of a region of interest within the body in which the probe is located. For example, a catheter may be inserted through the vascular system into the patient's heart while three-dimensional (3D) images of the heart are captured by MRI. Tracking apparatus, such as the above-mentioned CARTO magnetic tracking system, may meanwhile be used to track and indicate the location of the catheter in the body during diagnostic and therapeutic procedures that are carried out in this configuration.

To enable this sort of combined imaging and tracking functionality, a field transducer, for use in tracking the invasive probe, is placed in the bore of the imaging apparatus. When magnetic tracking is used, for example, the field transducer may have the form of a location pad, comprising multiple coils, and may be fixed below the movable bed of the imaging apparatus, on which the patient lies during the procedure. The location coordinates of the probe that are provided by the field transducer may be registered with the coordinate frame of the imaging apparatus so that the probe location can be indicated accurately on the 3D images. For this purpose, the field transducer is positioned so that the tracking volume that it defines overlaps with the imaging volume that is defined by the detector array inside the bore of the imaging apparatus.

For some procedures, however, limiting the tracking volume to the area of the bore of the imaging apparatus can be problematic. For example, in many cardiological procedures, a catheter is inserted into the body through the femoral vein and is advanced through the vascular system into the heart. The physician performing the procedure has a need to observe the location of the distal end of the catheter all the way from its entry point to the heart. The static tracking volume of the tracking apparatus in the bore of the imaging apparatus may not be sufficient for this purpose.

Embodiments of the present invention that are described herein overcome this limitation by making use of the existing movable bed of the imaging apparatus and of the registration between the respective coordinate frames of the imaging and tracking apparatuses in order to extend the effective tracking volume. These embodiments exploit the fact that the coordinates of the movable bed in the imaging apparatus are necessarily registered with the coordinate frame of the imaging apparatus itself, in order to enable the imaging apparatus to shift the patient's body precisely to the desired location during imaging. On this basis, the bed coordinates can be registered relative to the coordinate frame of the tracking apparatus, and a system controller may thus accurately determine the probe location relative to the bed.

On this basis, in the disclosed embodiments, the controller applies the location of the invasive probe that is indicated by the tracking apparatus in controlling the movable bed so as to transport the body of the patient in a desired manner through the imaging and tracking volumes of the combined system. The controller typically causes the movable bed to shift in response to motion of the invasive probe within the body of the patient so that the invasive probe remains within the tracking volume notwithstanding the motion of the probe. In other words, referring to the previous example in which a catheter is inserted through the femoral vein into the heart, the controller may control the bed initially to position the region of the patient's groin in the bore of the imaging system, and may thereafter cause the bed to shift in the direction opposite to the motion of the catheter as the catheter is advanced up through the veins to the heart. In this way, the catheter always remains within the tracking (and imaging) volume of the system. The controller may control the speed of movement of the bed precisely so as to compensate for advancement of the catheter through the body.

Thus, the disclosed embodiments take advantage of the existing features and capabilities of the imaging apparatus in order to enlarge the effective tracking volume of the tracking apparatus, far beyond the limited volume provided by the field transducer itself. The enlarged tracking volume provides the physician with accurate location information regarding the invasive probe throughout the patient's body at little or no added cost relative to the costs of the component imaging and tracking apparatuses. This location information may be provided to the physician by itself or in combination with images captured by the imaging apparatus at the different bed positions.

FIG. 1 is schematic pictorial illustration of an imaging and tracking system 20, in accordance with an embodiment of the present invention. In this example, system 20 is assumed to comprise imaging apparatus in the form of an MRI scanner 26. A physician 32 inserts an invasive probe in the form of a catheter 30 into the body of a patient 22, who lies on a movable bed 24 in scanner 26. Magnetic tracking apparatus, comprising a magnetic location pad 34 and suitable sensing coils (not shown) within catheter 30, provides an indication of the location of the catheter within the body. These particular components of system 20 are shown and described here, however, solely for the sake of concreteness and clarity of explanation, and the principles of the present invention may similarly be applied in systems using other imaging and tracking modalities, as well as other sorts of invasive probes and procedures.

As is known in the art, MRI scanner 26 comprises magnetic field coils (not shown), including field gradient coils, which generate a spatially-variant magnetic field within the scanner. In addition, scanner 26 comprises an array of detectors, in the form of transmit/receive coils 28. These coils radiate radio-frequency (RF) energy, which interacts with the nuclear spins of the patient's tissue, and detect RF signals received from the tissue as the nuclei relax. The detected signals are processed to generate 3D images of the region of the patient's body that is located inside an imaging volume 42 defined by coils 28. (The region between coils 28 is also referred to as the "bore" of scanner 26, in reference to the central cylindrical imaging zone in many imaging scanners.) Bed 24 may be shifted by scanner 26 so that the region of the body that is of interest is located in imaging volume 42.

While patient 22 lies on bed 24 in scanner 26, physician 32 feeds catheter 30 through the patient's vascular system from the femoral vein to the patient's heart 33. Location pad 34 serves as a field transducer to generate magnetic fields that are received by one or more sensing coils in the distal end of catheter 30. Alternatively, the coil or coils in the catheter may generate magnetic fields, which are sensed by location pad 34.

Location pad 34 may be fixed in scanner 26 below bed 24. To fit into these narrow confines, location pad 34 may comprise multiple low-profile coils (not shown), arranged in a horizontal plane within a housing made from an MRI-compatible material, such as a suitable plastic. When drive currents are applied to the coils, they generate magnetic fields that pass through bed 24 into the body of patient 22. Further details of this sort of location pad and its operation in tracking catheter 30 are described, for example, in U.S. patent application Ser. No. 14/138,654, filed Dec. 23, 2013, whose disclosure is incorporated herein by reference. Alternatively, other sorts of magnetic location pads may be used to similar effect.

A console 36 drives location pad 34 and receives signals from catheter 30 in response to the magnetic fields generated by the location pad. A controller 38 in console 36 processes these signals in order to derive location coordinates of catheter 30 inside the patient's body. The controller may compute these coordinates using the methods described in the above-mentioned U.S. patent application Ser. No. 14/138,654, or as is otherwise known in the art. The location coordinates provided in the frame of reference of location pad 34 are typically registered with the image coordinate frame of scanner 26, using a suitable calibration procedure, before bringing patient 22 into system 20. A calibration jig and procedure that may be used for this purpose are described, for example, in U.S. patent application Ser. No. 14/195,068, filed Mar. 3, 2014, whose disclosure is incorporated herein by reference.

Controller 38 also receives image data from MRI scanner 26 and is able to control certain functions of the scanner, such as movement of bed 24, using a real-time messaging protocol or application program interface (API) provided by scanner 26. Controller 38 is thus able to drive a display 40 on console 36 to show 3D images produced by scanner 26 and to superimpose an indication of the location of catheter 30, provided by the tracking apparatus, on these images. This superimposition is made possible by the above-mentioned registration between the coordinate frames of the tracking apparatus (specifically of location pad 34) and of scanner 26. On this basis, controller 38 may also derive 3D maps and local data from the signals output by catheter 30 and show these maps and data on display 40 in registration with the 3D images from scanner 26.

Controller 38 typically comprises a general-purpose computer processor, with suitable interfaces and software for carrying out the functions that are described herein. The software may be stored in non-transitory computer-readable media, such as optical, magnetic, or electronic memory media. Alternatively or additionally, at least some of the functions of controller 38 may be carried out by suitable logic (hard-wired or programmable) or by a programmable digital signal processor.

Figure 2A:
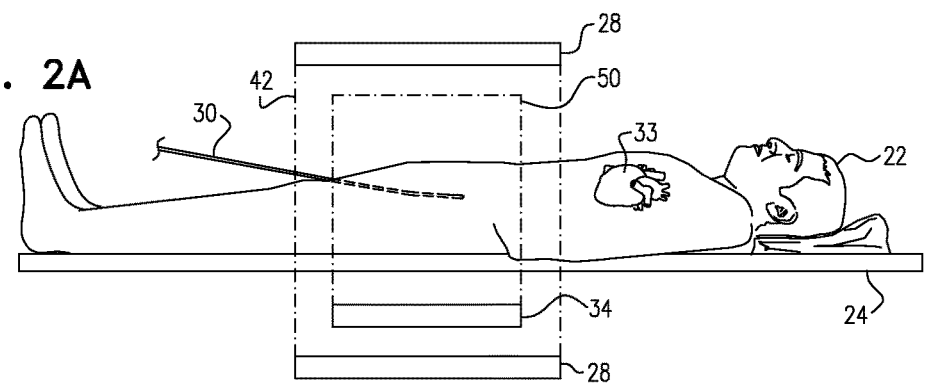
FIGS. 2A and 2B are schematic side views of a patient in an imaging and tracking system, in accordance with an embodiment of the present invention.
Figure 2B:
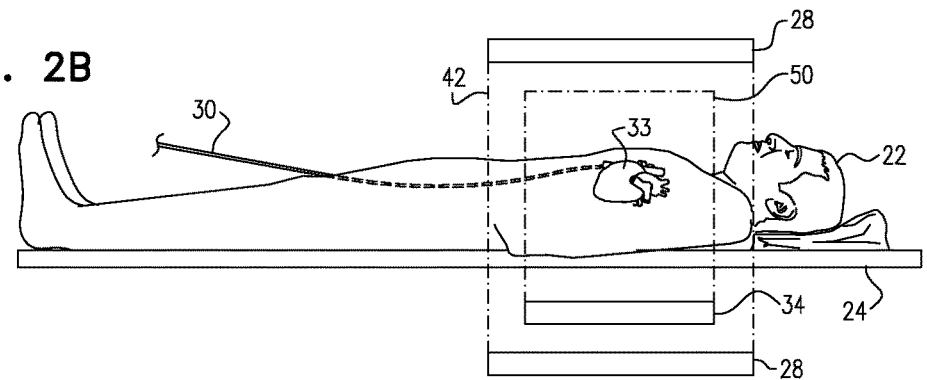

FIGS. 2A and 2B are schematic side views of patient 22 on bed 24 in system 20, at two successive stages in the catheterization procedure illustrated in FIG. 1, in accordance with an embodiment of the present invention. These figures illustrate how controller 38 is able to effectively extend a tracking volume 50 of location pad 34 by suitably controlling the movement of bed 24.

The size and extent of tracking volume 50 are determined generally by the size and position of location pad 34 within scanner 26. Typically, as illustrated in FIGS. 2A and 2B, location pad 34 is positioned so that tracking volume 50 overlaps imaging volume 42 (thus facilitating the presentation of registered data, as described above). The geometrical constraints of scanner 26 and location pad 34 generally make it infeasible to extend tracking volume 50 much beyond the bounds of imaging volume 42. Consequently, as illustrated in FIG. 2B, tracking volume 50 is typically large enough to encompass an area of the thorax of patient 22 that contains heart 33 while scanner 26 images this area, but cannot concurrently encompass the area of the patient's groin and abdomen through which catheter 30 is inserted into the body.

To remedy this problem, while physician 32 is inserting and advancing catheter 30 through the veins in the groin and abdomen, controller 38 instructs scanner 26 to shift bed 24 so that the groin and abdomen of patient 22 are located in tracking volume 50 of location pad 34, as shown in FIG. 2A. Controller 38 is thus able to track the location of catheter 30 during this stage. (Scanner 26 may optionally be operated to capture images of this region of the body, as well, if desired.) As physician 32 advances catheter 30 toward heart 33, controller 38 tracks the movement of the catheter and instructs scanner 26 to shift bed 24 in the opposite direction, so that the catheter remains within tracking volume 50 notwithstanding the movement, until the catheter reaches heart 33 as shown in FIG. 2B.

Consequently, the effective tracking volume of the tracking apparatus in system 20 is considerably larger than the actual, physical tracking volume 50 provided by location pad 34, and includes both the abdomen (FIG. 2A) and the thorax (FIG. 2B) of patient 22. When physician 32 withdraws catheter 30 from the body, controller 38 may cause bed 24 to move back in the opposite direction in order to track the exit path of the catheter through the vascular system.

Figure 3:
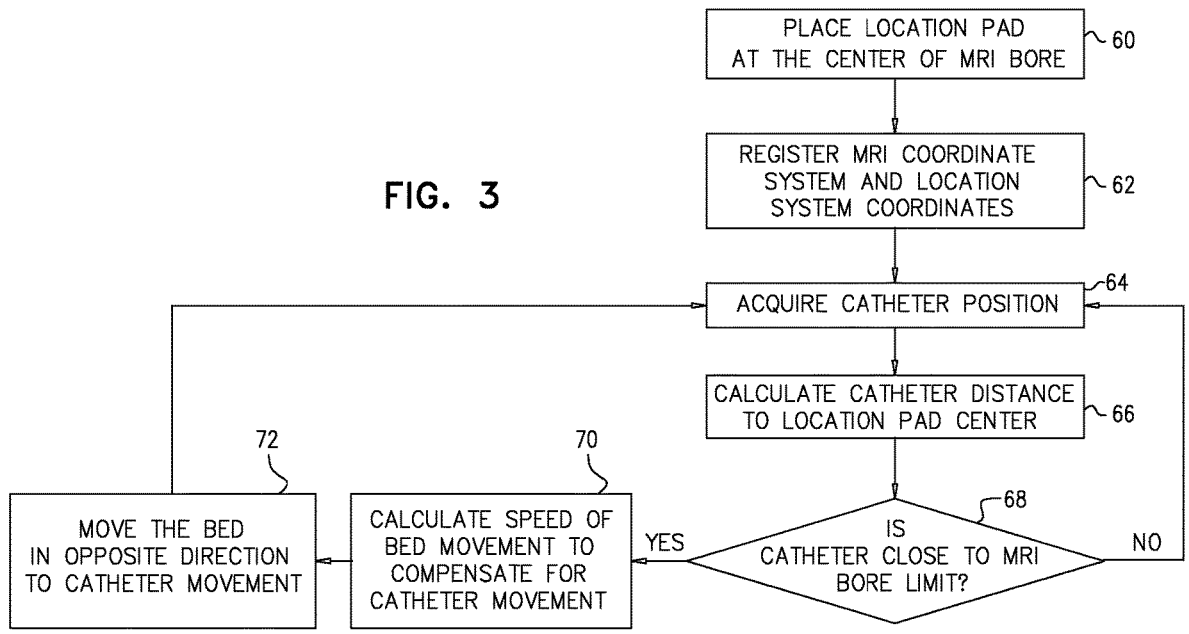
FIG. 3 is a flow chart that schematically illustrates a method for controlling the movement of a patient bed in an imaging and tracking system, in accordance with an embodiment of the present invention.

FIG. 3 is a flow chart that schematically illustrates a method for controlling the movement of bed 24 in system 20, in accordance with an embodiment of the present invention. As noted earlier, although this method is described, for the sake of clarity, with specific reference to the elements of system 20, it may similarly be applied in other systems with other sorts of imaging and tracking capabilities. The method implements a closed-loop control algorithm to shift the position of bed 24 relative to location pad 34, and thus to move patient 22 in such a manner that the distal end of catheter 30 will always stay in tracking volume 50, as well as in imaging volume 42.

As an initial step, location pad 34 is placed in the center of the "bore" of MRI scanner 26, at a pad placement step 60. In other words, location pad 34 is positioned so that its tracking volume 50 overlaps imaging volume 42, as described above. Controller 38 registers the image coordinate system of scanner 26 with the location coordinate system of location pad 34, at a registration step 62. In this manner, location-based data relating to catheter 30 may be superimposed on images generated by scanner 26, and controller 38 may also use the catheter location in controlling the position of bed 24.

Based on the signals generated by interaction of catheter 30 with location pad 34, controller 38 acquires the current location coordinates of the catheter, at a position acquisition step 64. Controller 38 then calculates the distance between the distal end of catheter 30 and the center of location pad 34 (or equivalently, the center of tracking volume 50), at a distance calculation step 66. The controller evaluates this distance to determine whether the catheter is near the center of tracking volume 50 or close to its edge, at a location checking step 68. As long as the catheter is at least some threshold distance away from the edges of the tracking volume, controller 38 returns to step 64 without invoking any movement of bed 34.

Upon finding at step 68 that the distal end of catheter 30 is close to an edge of tracking volume 50, however, controller 38 invokes corrective movement of bed 34. For this purpose, controller 38 may calculate the speed of bed movement that will best compensate for the movement of catheter 30 through the body of patient 22, at a speed calculation 70. This speed may be related, for example, to the speed at which physician 32 is advancing or retracting the catheter through the vascular system. Controller 38 instructs scanner 26 to shift bed 24 at the appropriate speed in the direction opposite to the direction of catheter motion, at a bed movement step 72.

Controller 38 then returns to step 64, and the process continues iteratively until the procedure is completed.

As noted earlier, although the embodiments described above relate to magnetic tracking of a catheter in an MRI-based system, the principles of the present invention may similarly be applied using other imaging modalities in which the patient is transported through the imaging apparatus by a movable bed. For example, in alternative embodiments (not shown in the figures), an invasive probe may be tracked in the manner described herein in conjunction with CT, PET, SPECT or other imaging modalities that are known in the art. Additionally or alternatively, the probe location may be tracked, mutatis mutandis, using other technologies that are known in the art, such as ultrasonic or electrical tracking techniques. The principles of the present invention may be applied not only in cardiac catheterization, but also in tracking invasive probes of other types in diagnostic and therapeutic procedures applied to other organs.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical imaging and tracking system with an effective tracking volume and a physical tracking volume, the effective tracking volume being greater than the physical tracking volume, comprising:
    an imaging apparatus comprising an array of detectors defining an imaging volume, the imaging apparatus configured to provide images of a region of interest of the body of a patient when said region of interest is within the imaging volume;
    a movable bed configured to transport the body of the patient in response to a controller from a location outside the imaging volume through the imaging volume;
    an invasive probe configured for insertion into a lumen within the body of the patient and having a distal end;
    a tracking apparatus comprising a field transducer located within the imaging apparatus and configured for defining the physical tracking volume within the imaging apparatus, and for generating location data of the invasive probe within the tracking volume, said location data being determined by the interaction between the field transducer and the invasive probe; and
    the controller operatively linked to the tracking apparatus and to the movable bed, the controller being configured to receive location data indicating the location of the invasive probe within the tracking volume,
    the controller further configured to implement a closed-loop control algorithm to shift the position of the bed relative to the location pad during movement of the distal end in the lumen in such a manner that the distal end will always stay within both the physical tracking volume and the imaging volume during said movement of the distal end, thereby creating the effective tracking volume greater than the physical tracking volume.

2. The system according to claim 1, wherein the imaging apparatus comprises a magnetic resonance imaging apparatus configured to receive signals from tissues in the body in response to an applied magnetic field.

3. The system according to claim 1, wherein the invasive probe comprises a catheter, which is configured for insertion through a blood vessel into a heart of the patient.

4. The system according to claim 1,
    wherein the tracking apparatus comprises a location pad having a plurality of coils configured to generate magnetic fields within the physical tracking volume, and
    wherein the tracking apparatus is configured to receive signals output from the invasive probe in response to the magnetic fields, and to process the signals in order to determine and display the location of the invasive probe.

5. The system according to claim 4, wherein the field transducer is positioned so that the physical tracking volume overlaps the imaging volume and wherein the controller is configured to register the location of the invasive probe in a coordinate system of the imaging apparatus and to superimpose an indication of the registered location on the images that are produced by the imaging apparatus.

6. The system according to claim 1,
    wherein the movable bed is movable along a single horizontal axis which is within the imaging apparatus and extends through both the physical tracking volume and the imaging volume and wherein the physical tracking volume and the imaging volume are fixed and overlap.

7. The system according to claim 6, wherein the controller is configured to cause the movable bed to shift in a direction opposite to the motion of the invasive probe.

8. The system according to claim 7, wherein the controller is configured to control a speed of movement of the movable bed so as to compensate for advancement of the invasive probe through the body.

9. A method for imaging and tracking an invasive probe in the body of a patient for providing an effective tracking volume greater than a physical tracking volume, the method comprising:
providing an imaging apparatus having an imaging volume, a tracking apparatus comprising a field transducer and having a physical tracking volume, an invasive probe having a distal end, a display, and an automatically movable bed;
wherein the tracking apparatus is located within the imaging apparatus;
wherein the physical tracking volume is fixed relative to the imaging volume;
inserting the invasive probe into a lumen of the patient on the moveable bed, and moving the invasive probe within the patient;
creating an image of a portion of the patient having the invasive probe therein using the imaging apparatus, and displaying the image on the display;
tracking a location of the invasive probe with the field transducer while the invasive probe is moved within the patient by determining the interaction between the field transducer and the invasive probe;
automatically moving the movable bed into the imaging volume in response to the tracking apparatus detecting that the invasive probe may be leaving the physical tracking volume;
controlling the speed and direction of the movable bed by a closed-loop control algorithm to shift the position of the bed relative to the location pad during movement of the distal end in the lumen in such a manner that the distal end will always stay within both the physical tracking volume and the imaging volume during said movement of the distal end, thereby creating the effective tracking volume greater than the physical tracking volume.

10. The method according to claim 9, wherein the imaging apparatus comprises a magnetic resonance imaging apparatus.

11. The method according to claim 9, wherein the invasive probe comprises a catheter,
the method comprising inserting the catheter into the patient and moving the catheter into a heart of the patient.

12. The method according to claim 9, wherein the tracking apparatus comprises the field transducer which comprises a location pad;
the method further comprising generating magnetic fields within the physical tracking volume;
wherein the step of tracking the location of the invasive probe comprises receiving signals output by the invasive probe in response to said magnetic fields, and processing the signals from the invasive probe to determine a location of the invasive probe.

13. The method according to claim 12, wherein the field transducer is positioned so that the physical tracking volume overlaps the imaging volume, and wherein controlling the movable bed comprises registering the location of the invasive probe in a coordinate system of the imaging apparatus, and superimposing an indication of the registered location on the images that are produced by the imaging apparatus.

14. The method according to claim 9, wherein the tracking volume and the physical imaging volume overlap;
the method comprising:
moving the invasive probe through a femoral vein of the patient towards and into a heart of the patient; and
automatically moving the movable bed and the patient horizontally through the imaging volume and the tracking volume in response to said movement of the invasive probe through the femoral vein towards the heart, said movement maintaining the invasive probe within both the physical tracking volume and the imaging volume.

15. The method according to claim 14, the method further comprising:
detecting movement of the invasive probe in a first direction when the invasive probe is close to the edge of the physical tracking volume located and in response to said detection, moving the movable bed in a second direction opposite the first direction so that the catheter remains within the physical tracking volume.

16. The method according to claim 15, wherein moving the movable bed comprises controlling a speed of movement of the movable bed so as to compensate for advancement of the invasive probe through the body.

17. A controller for use with a medical imaging system for providing the system with an effective tracking volume greater than a physical tracking volume:
wherein the controller comprises a general purpose computer having interfaces and software;
wherein the controller is configured for operational connection and use with other components of the medical imaging system, said other components comprising:
an imaging apparatus comprising an array of detectors and having an imaging volume, the imaging apparatus being adapted to provide images of a region of interest of a body of a patient when said region of interest is within the imaging volume;
a movable bed configured to automatically transport the body of the patient when present, through the imaging volume;
an invasive probe having a distal end and configured for insertion into a lumen of the body of the patient;
a tracking apparatus comprising a field transducer located within the imaging apparatus and configured for defining a physical tracking volume within the imaging apparatus and being configured to determine location data for the invasive probe when the probe is in the body of the patient based on an interaction between the field transducer and the invasive probe;
wherein the controller is configured to control the following steps when the controller is operationally connected to said imaging apparatus, movable bed, invasive probe, and tracking apparatus:
receive location data indicating that the invasive probe may be leaving the physical tracking volume;
in response to receiving said location data indicating the invasive probe may be leaving the physical tracking volume, to automatically move the movable bed so as to maintain the invasive probe within the tracking volume of the imaging apparatus; and
when automatically moving the movable bed, controlling the speed and direction of the movable bed by a closed-loop control algorithm to shift the position of the bed relative to the location pad during movement of the distal end in the lumen in such a manner that the distal end will always stay within both the physical tracking volume and the imaging volume during said movement of the distal end, thereby creating the effective tracking volume greater than the physical tracking volume.

18. The controller according to claim 17, wherein the invasive probe comprises a cardiac catheter, wherein the imaging apparatus comprises a magnetic resonance imaging apparatus, and wherein the movable bed is horizontally movable through the magnetic resonance imaging apparatus.

19. The controller according to claim 18, wherein the controller is configured to cause the movable bed to shift in a direction opposite to the direction in which the invasive probe had previously moved inside the body.

20. The controller according to claim 19, wherein the controller is configured to control a speed of movement of the movable bed so as to compensate for advancement of the invasive probe through the body.

21. The system according to claim 1 wherein the controller is configured to cause the moveable bed to move in a direction opposite the direction in which the invasion probe had previously moved inside the body.

22. The method according to claim 9 wherein the moveable bed is moved in a direction opposite the direction in which the invasion probe had previously moved within the body.

23. The method according to claim 9 wherein the speed of movement of the moveable bed is controlled to compensate for advancement of the invasion probe within the patient.

24. The system according to claim 1, wherein the location data indicating that the invasive probe may be leaving the physical tracking volume is location data that the invasive probe is close to the edge of the physical tracking volume.

25. The method according to claim 9, wherein detecting that the invasive probe may be leaving the imaging volume comprises detecting that the invasive probe is close to the edge of the physical tracking volume.

26. The controller according to claim 17, wherein the location data comprises location data indicating that the invasive probe is close to the edge of the physical tracking volume.

* * * * *